United States Patent [19]

Capanna

[11] Patent Number: 5,330,531
[45] Date of Patent: Jul. 19, 1994

[54] HUMERAL ENDOPROSTHESIS

[75] Inventor: Rudolfo Capanna, Bologna, Italy

[73] Assignee: Howmedica GmbH, Schönkirchen, Fed. Rep. of Germany

[21] Appl. No.: 985,085

[22] Filed: Dec. 2, 1992

[30] Foreign Application Priority Data

Dec. 10, 1991 [DE] Fed. Rep. of Germany ... 9115283[U]

[51] Int. Cl.$^5$ .............................................. A61F 2/40
[52] U.S. Cl. ........................................ 623/19; 623/18
[58] Field of Search ..................... 623/16, 18, 19, 23

[56] References Cited

U.S. PATENT DOCUMENTS

| | | | |
|---|---|---|---|
| 3,979,778 | 9/1976 | Stroot | 623/19 |
| 4,187,559 | 2/1980 | Grell et al. | 623/18 |
| 4,355,427 | 10/1982 | Schneider | 623/19 |
| 4,578,081 | 3/1986 | Harder et al. | 623/18 |
| 4,921,500 | 5/1990 | Averill et al. | 623/18 |

FOREIGN PATENT DOCUMENTS

| | | |
|---|---|---|
| 0381588 | 8/1990 | European Pat. Off. . |
| 3406358 | 12/1984 | Fed. Rep. of Germany . |
| 8814434 | 3/1989 | Fed. Rep. of Germany . |
| 9115283 | 2/1992 | Fed. Rep. of Germany . |

OTHER PUBLICATIONS

Richards "H-J-B Shoulder Prosthesis" Journal Bone & Joint Surgery, Mar. 1964 vol. 46-A p. 17.

*Primary Examiner*—David Isabella
*Attorney, Agent, or Firm*—Peter C. Richardson; Lawrence C. Akers; Raymond W. Augustin

[57] ABSTRACT

A humeral endoprosthesis for partially or completely replacing the humerus has a spherical head portion which is connected to an elongate distal shaft portion. The spherical head includes openings for fixing a number of ligaments. Distally of the opening a groove is formed around the circumference of the head for receiving a band made of body compatible material.

8 Claims, 4 Drawing Sheets

5,330,531

HUMERAL ENDOPROSTHESIS

BACKGROUND OF THE INVENTION

1. Field of the Invention

The present invention relates to an endoprosthesis for partly or completely replacing the humerus. More particularly, it relates to a humeral prosthesis adapted to be easily connected to the shoulder ligament.

2. Description of the Prior Art

A humeral endoprosthesis is disclosed in German Patent DE-GM 88 14 434. This endoprosthesis comprises a humerus head portion having a distal end including an inner cone. For a complete replacement, the humeral head portion is connected to a shaft comprising a pair of elongate shaft portions which may be axially connected to each other and which shaft is secured to the distal joint portion through a tapered joint. For a partial replacement the distal end of the shaft is connected to a portion of the humerus not resected. Below the spherical head of the head portion a number of openings are provided for securing bands or, respectively, tissue portions forming the articulate capsule.

SUMMARY OF THE INVENTION

It is the object of the invention to provide an endoprosthesis for partly or completely replacing the humerus, which endoprosthesis is designed to provide for a particular suitable connection of the ligaments of the shoulder joint to the prosthesis.

The head of the endoprosthesis according to the present invention comprises an at least partly peripherally extending groove located distally of the largest diameter for receiving a band extending around the head. The ends of the ligaments or the tissue forming the articular capsule can be safely fixed in the groove by a band made of body compatible material such as dacron. According to an embodiment of the invention, the groove is located in a meridian plane of the head. The groove is thus positioned to provide optimum conditions for fixing the tissue and the bands.

According to a further embodiment of the invention, the openings are located in a meridian plane adjacent to the groove, i.e. positioned towards the pole of the head with respect to the groove. Additional securing ligaments may be drawn through the openings.

The head and the portion extending therefrom up to the cone of the known prosthesis are solid. Thus, this portion of the prosthesis has a substantial weight. According to a further embodiment of the invention it is preferred to provide a short and hollow shaft portion integrally formed on the head. For connecting the shaft portion extending therefrom, the head prosthesis portion comprises either an inner cone or an inner threaded portion wherein the shaft portion comprises a corresponding outer cone or an outer threaded portion.

According to yet an additional embodiment of the invention, the cavity of the hollow head contains a wall including a threaded bore for receiving a threaded pin for connecting the head portion and the shaft portion. The screw pin is provided to extend distally through the shaft portion when connecting the head and shaft portion to be screwed into the head portion.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
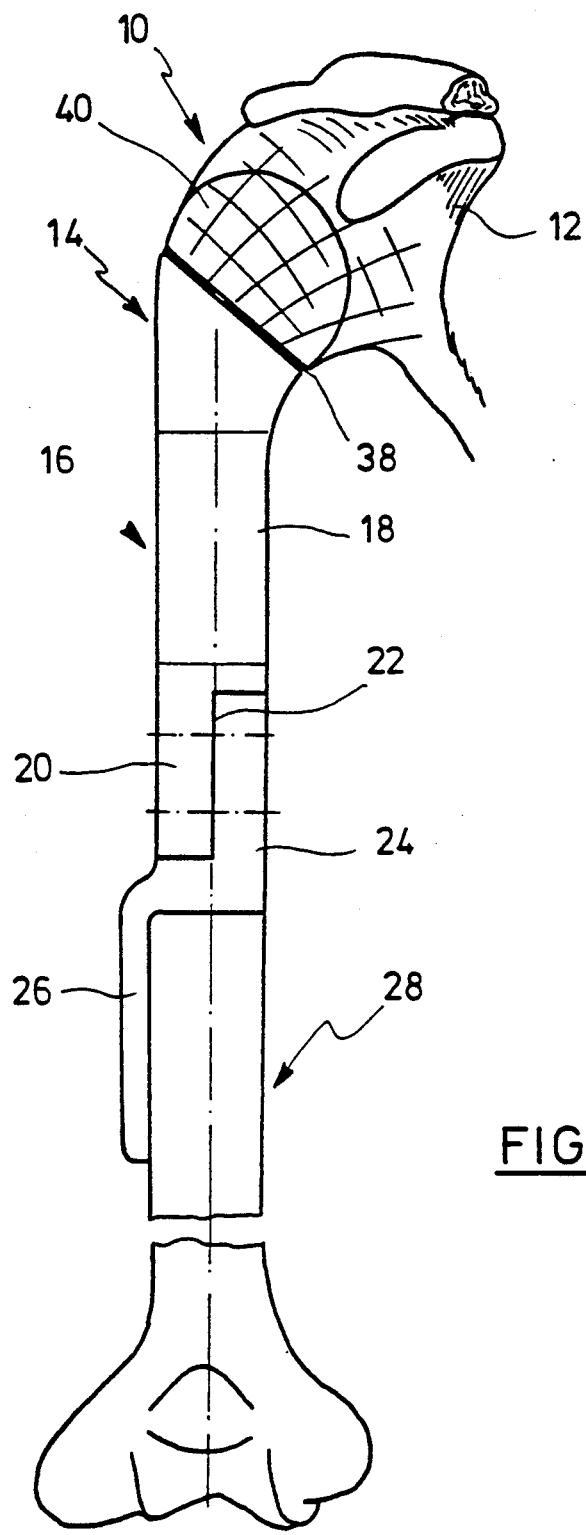
FIG. 1 is a side view of an endoprosthesis according to the invention for partly replacing a humerus.

The preferred shoulder joint 10, shown in FIG. 1, is formed by a natural shoulder blade 12 including an artificial articulate capsule, for example, and a head portion 14 of an endoprosthesis 16. The head portion 14 to be formed as a rotational head is attached to a shaft portion 18 including a stepped end 20 with a flat 22 cooperating with an end portion 24 of a distal shaft portion, which comprises similar flats cooperating with flat 22, wherein the portions are to be connected to each other by screws. A connection of this type is disclosed in DE-GM 88 14 434. The distal shaft portion includes a lateral strut 26 to be secured to the distal portion 28 of a natural humerus.

Figure 2:
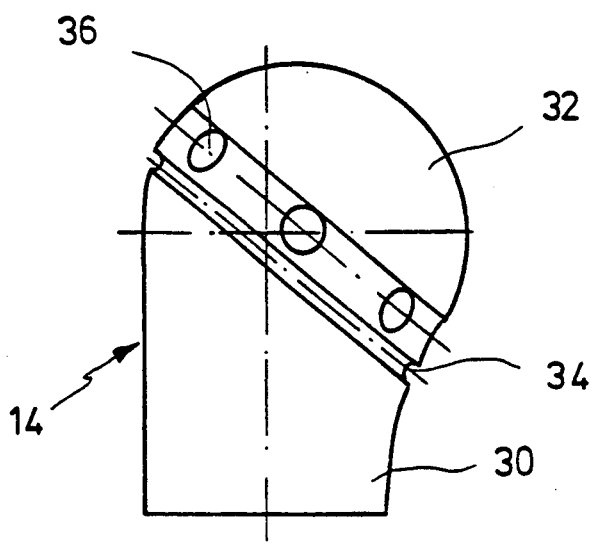
FIG. 2 is an embodiment of a head portion of a humerus endoprosthesis according to the invention.

The preferred head portion 14 is shown in detail in FIG. 2. The head includes a distal shaft portion 30 which proximally ends in a spherical head 32 under an angle corresponding to the anatomic conditions of the humerus. As seen from FIG. 2, the joint between shaft portion 30 and head 32 includes an annular groove 34 having an arcuate or circular cross-section. Groove 34 is located in a meridian plane with respect to head 32, which is located distally below the maximum meridian plane at the equator of the spherical head. A number of openings 36 are formed in the head 32 in the plane of the maximum diameter or, respectively, the maximum meridian plane.

As FIG. 1 shows, the groove 34 receives a body compatible band 38 which is slung around the end portion of bands and capsule tissue to fix these parts to the head portion 14. Ligaments and capsule tissue are indicated at 40. Openings 36 serve to receive further ligaments or the like to improve the connection.

Figure 3:
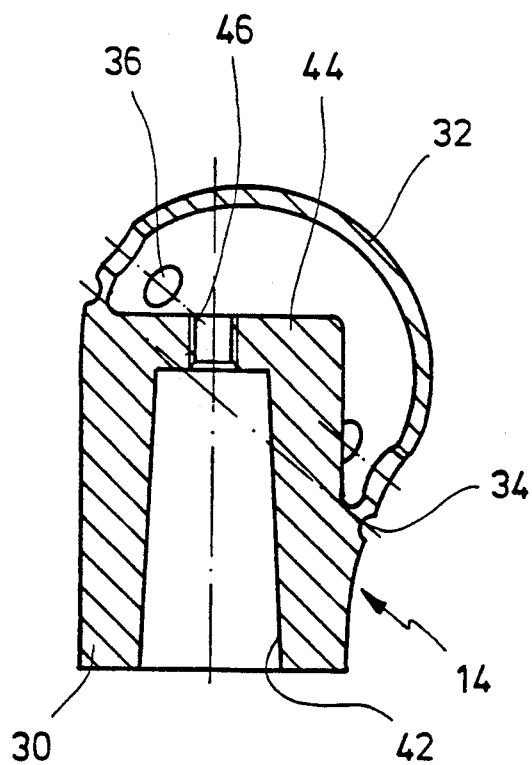
FIG. 3 is a longitudinal section through the head portion of FIG. 2.

FIG. 3 shows the longitudinal section through the head portion 14 of FIG. 2. Distal shaft portion 30 includes an inner cone 42 to receive an outer cone of the shaft portion 18 (FIG. 1). The wall of the shaft portion 30 limiting the inner cone 42 extends partly into the hollow head 32. Thus, a cross wall 44 is formed in which a threaded bore 46 is provided coaxially with respect to the shaft portion 30. The threaded bore 46 receives a threaded pin (not shown) which extends distally through the shaft portion 18 and is screwed in the threaded bore 46 to fix the head portion 14 and the shaft portion 16 with respect to each other.

Figure 4:
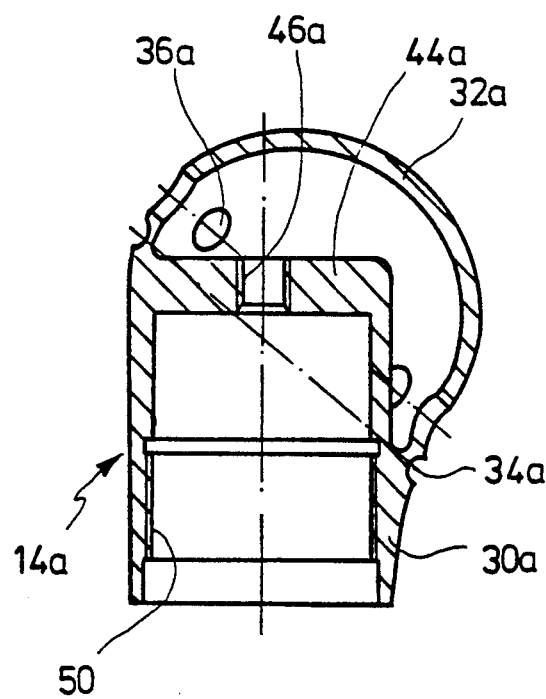
FIG. 4 is a longitudinal section through a further embodiment of a head portion.

The embodiment shown in FIG. 4 differs slightly from that shown in FIG. 3. With respect to FIG. 3, identical parts bear the same reference numerals but an "a" is added for clarity. The distal shaft portion 30a comprises a threaded bore 50 to receive an outer threaded portion of a shaft portion similar to the shaft portion 18 shown in FIG. 1. The threaded bore 46a receives a threaded pin to fix a shaft portion (not shown) to the head portion 14a.

Figure 5:
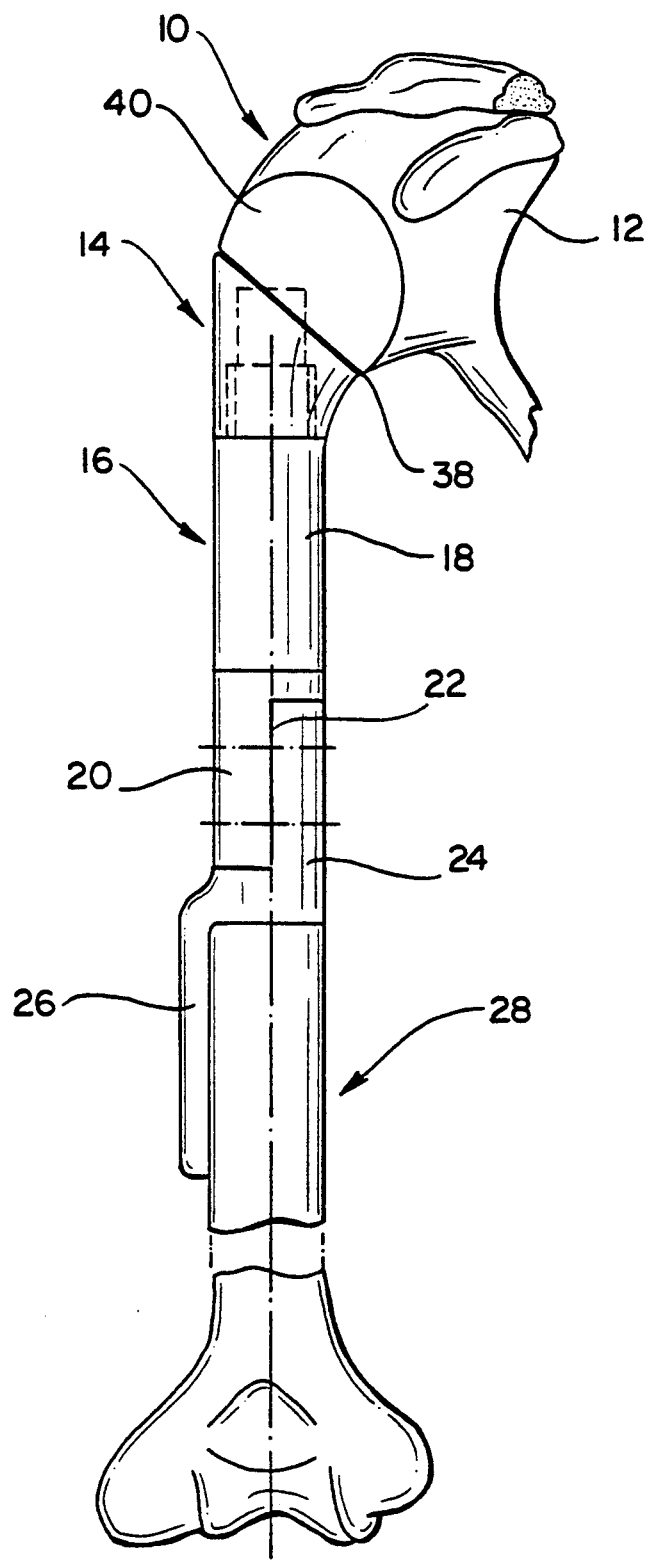
FIG. 5 is a side view of an embodiment of the endoprosthesis of the present invention with a threaded end.
Figure 6:
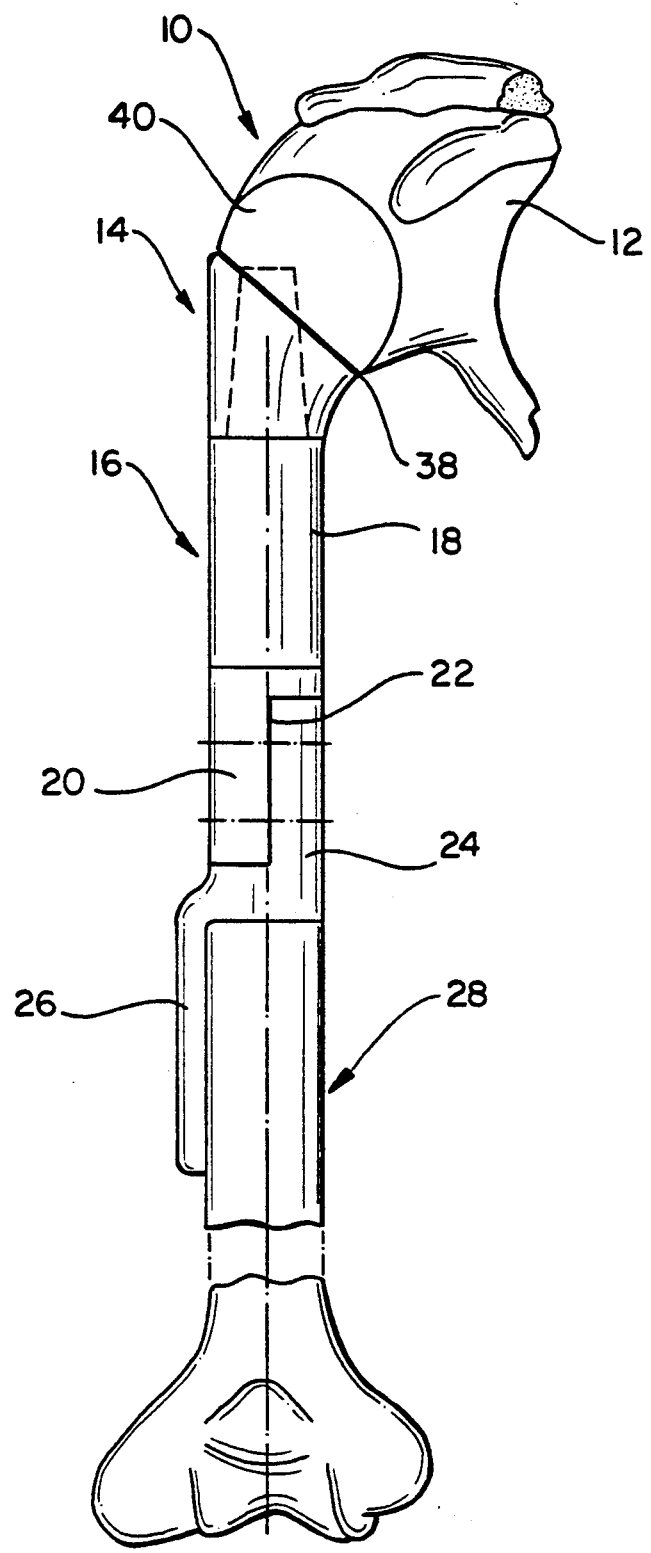
FIG. 6 is a side view of an embodiment of the endoprosthesis of the present invention with a conical end.

FIGS. 5 and 6 show embodiments of the present invention adapted to mate with the head portions shown in FIGS. 4 and 3 respectively. FIG. 5 shows a male threaded extension 60 for coupling with threaded bore 30 of head portion and FIG. 6 shows a male conical trunion 62 for mating with conical recess 42 of head portion.

While several examples of the present invention have been described, it is obvious that many changes and modifications may be made thereunto, without departing from the spirit and scope of the invention.

I claim:

1. An endoprosthesis for partly or completely replacing the humerus comprising a spherical head portion having means for connecting said head portion to an elongate distal shaft portion, wherein the spherical head includes openings lying in a meridian plane for fixing a number of ligaments and includes at least a partly circumferential groove extending in a meridian plane distally below an equator of the spherical head to receive a band made of body compatible material wrapped therearound and wherein said head has a hollow inner cavity including a cross wall, said connecting means including a threaded bore in said cross wall for receiving a threaded pin to connect the head portion to the distal shaft portion.

2. The endoprosthesis of claim 3 wherein a hollow shaft portion extends from the head.

3. The endoprosthesis of claim 2 wherein the connecting means is on the hollow shaft portion and further comprises a female conical opening to receive an outer cone of a distal shaft portion.

4. The endoprosthesis of claim 2 wherein the connecting means is on the hollow shaft portion and further comprises an inner thread cooperating with an outer threaded portion of said distal shaft portion.

5. A humeral endoprosthesis comprising:
a shaft portion having a proximal and distal end;
a generally hemispherical head portion including means for coupling said head portion to the proximal end of said shaft portion, said head portion having at least two openings located adjacent the equator thereof for receiving ligaments and having a circumferential groove located in a meridian plane distally of said equator and wherein said head has a hollow inner cavity including a cross wall, said Coupling means including a threaded bore in said cross wall for receiving a threaded pin to connect the head portion to the shaft portion.

6. The endoprosthesis of claim 5 wherein said coupling means on said head portion further comprises a female conical opening to receive an outer cone of a distal shaft portion.

7. The endoprosthesis of claim 5 wherein said coupling means on said head portion further comprises an inner thread cooperating with an outer threaded portion of said distal shaft portion.

8. An endoprosthesis for partially or completely replacing the humerus comprising:
a shaft portion having a proximal and distal end;
a hollow, generally hemispherical head portion including means for coupling said head portion to the proximal end of said shaft portion, a circumferential groove having a generally U-shaped cross section extending around the head portion in a meridian plane distally of an equator of said hemispherical head portion and said head portion having at least two openings into said hollow head portion located in a meridian plane adjacent the equator for receiving ligaments.

* * * * *